United States Patent [19]

Hoffman, Jr. et al.

[11] Patent Number: 4,505,923

[45] Date of Patent: Mar. 19, 1985

[54] ETHERS OF HYDROXYBENZOTHIAZOLE-2-SULFONAMIDE FOR THE TOPICAL TREATMENT OF ELEVATED INTRAOCULAR PRESSURE

[75] Inventors: Jacob M. Hoffman, Jr., North Wales; Otto W. Woltersdorf, Jr., Chalfont, both of Pa.

[73] Assignee: Merck & Co., Inc., Rahway, N.J.

[21] Appl. No.: 547,189

[22] Filed: Oct. 31, 1983

[51] Int. Cl.$^3$ ............... C07D 277/80; A61K 31/425
[52] U.S. Cl. .................... 514/229; 514/326; 514/367; 514/912; 544/135; 546/209; 548/166
[58] Field of Search ............ 424/270, 248.51, 267; 544/135; 546/209; 548/166

[56] References Cited

U.S. PATENT DOCUMENTS 4,386,098  5/1983  Woltersdorf ............... 424/270
4,416,890  11/1983 Woltersdorf ............... 424/270

OTHER PUBLICATIONS

Merck Index, 9th Edition, Entry 3682, p. 494.

Primary Examiner—Robert Gerstl
Attorney, Agent, or Firm—William H. Nicholson

[57] ABSTRACT

Novel ethers of hydroxy-2-benzothiazolesulfonamide are useful for the topical treatment of elevated intraocular pressure. Ophthalmic compositions include drops and inserts.

9 Claims, No Drawings

ETHERS OF HYDROXYBENZOTHIAZOLE-2-SULFONAMIDE FOR THE TOPICAL TREATMENT OF ELEVATED INTRAOCULAR PRESSURE

SUMMARY OF THE INVENTION

This invention relates to novel ethers of hydroxy-2-benzothiazolesulfonamide which are useful in the reduction of elevated intraocular pressure. More particularly this invention relates to the ethers having the structural formula:

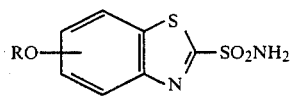

and to their use in the treatment of elevated intraocular pressure. This invention also relates to ophthalmic compositions that are employed in the treatment of elevated intraocular pressure, especially when accompanied by pathological damage such as in the disease known as glaucoma.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage of characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use.

(S)-1-tert-butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and β-blocking agents reduce intraocular pressure, none of these drugs manifests its action by inhibiting the enzyme carbonic anhydrase and, thereby, impeding the contribution made by the carbonic anhydrase pathway to aqueous humor formation.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in European Patent application No. 0,070,239 and 0,079,269 and U.S. application, Ser. No. 364,953. The compounds reported therein are 5 (and 6)-hydroxy-2-benzothiazolesulfonamides and acyl esters thereof.

DETAILED DESCRIPTION OF THE INVENTION

The novel compound of this invention has the structural formula:

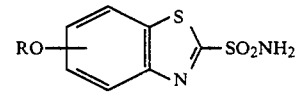

or a pharmaceutically acceptable salt thereof, wherein R is
(1) $C_{1-5}$alkyl substituted with one or more of:
  (a) hydroxy,
  (b) $C_{1-3}$alkoxy,
  (c) halo, such as chloro, bromo, or fluoro,
  (d)

wherein $R^1$ and $R^2$ are independently selected from
  (1) hydrogen,
  (2) $C_{1-5}$alkyl or
  (3) $R^1$ and $R^2$ joined together directly or through a heteroatom selected from O, N or S to form a 5 or 6-membered heterocycle with the nitrogen to which they are attached such as pyrrolidino, piperidino, morpholino, or thiazolidino
  (e) $C_{2-4}$alkanoyloxy such as acetoxy or butyloxy,
  (f) oxiranyl,
  (g) carboxy, or
  (h) $C_{1-3}$alkoxycarbonyl; or
(2) $C_{2-5}$alkenyl.

In the novel process of this invention the ethers of hydroxy-2-sulfamoylbenzothiazole are readily prepared by treatment of the corresponding hydroxy compound with the alkyl or alkenyl halide such as chloride, bromide or iodide in a polar solvent such as dimethylformamide, hexamethylphosphoramide, or the like in the presence of base such as an alkali metal alkoxide, preferably sodium methoxide, at about 0° C. to 35° C., usually about room temperature for about 10 to 30 hours.

An alternate synthesis of ethers comprises protecting the sulfonamide group as an N,N-disubstituted formamidine which is subsequently removed after formation of the desired ether. The formamidine derivative is prepared by adding, for example, N,N-dimethylformamide dimethyl acetal to a suspension of the hydroxybenzothiazole-2-sulfonamide in an inert organic solvent such as acetonitrile at about −10 to +60° C., preferably room temperature for about 0.5 to about 3 hours.

The ethers are then readily prepared by treating the protected hydroxy compound with the alkyl or alkenyl halide in a solvent such as dimethyl sulfoxide preferably in the presence of an acid acceptor such as potassium carbonate or the like, pyridine or the like or basic ion exchange resin. The reaction is conducted at about 25° to 100° C. preferably about 60° C., for about 10 to 36 hours, preferably about 18 hours.

The protecting group is then removed by treating the compound with dilute alkali such as 2N sodium hydroxide at about 20° to 60° C., preferably about 40° C. for about 0.5 to 3 hours, preferably about 1 hour.

Other processes for preparation of specific compounds of this invention are disclosed in the detailed Examples.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose is satisfactory.

When administered for the treatment of elevated intraocular pressure or glaucoma, the active compound is most desireably administered topically to the eye, although systemic treatment is also possible.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included When given by the topical route, the active drug is formulated into an ophthalmic preparation.

In such formulations, from 0.1% to 15% by weight can be employed. The objective is to administer a dose of from 0.1 to 10 mg per eye per day to the patient, with treatment continuing so long as the condition persists.

The active drug of this invention is most suitably administered in the form of ophthalmic pharmaceutical compositions adapted for topical administration to the eye such as a suspension, solution, ointment, or as a solid polymeric insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

EXAMPLE 1

6-(Allyloxy)benzothiazole-2-sulfonamide

A solution of sodium hydroxide (8.0 gm, 0.2 ml) in methanol (170 mL) was added dropwise to a solution of 6-hydroxybenzothiazole-2-sulfonamide (23.0 gm, 0.1 mol) and allyl bromide (10.0 mL, 0.12 mol) in dry dimethylformamide (100 mL). This mixture was stirred at room temperature for 16-20 hours and then poured into hydrochloric acid-ice water. The precipitate was collected by filtration, dissolved in ethyl acetate, washed with water, dried ($Na_2SO_4$) and evaporated. This residue was triturated with methylene chloride and the crystalline product was collected. (wt. 9.9 gm), m.p. 184°-187° C. A sample was recrystallized from 1,2-dichloroethane, m.p. 193°-195° C.

Analysis calculated for $C_{10}H_{10}N_2O_3S_2$: C, 44.43; N, 10.36; H, 3.73. Found: C, 44.45; N, 10.33; H, 3.78.

EXAMPLE 2

6-Allyloxybenzothiazole-2-sulfonamide

Step A:
N,N-Dimethyl-N'-(6-hydroxybenzothiazole-2-sulfonyl)formamidine

N,N-Dimethylformamide dimethyl acetal (1.5 mL, 11.3 mmol) was added to a partial suspension of 6-hydroxybenzothiazole-2-sulfonamide (2.3 gm, 10 mmol) in acetonitrile (20 mL) to give an immediate solution. After stirring at room temperature for 1 hour, the reaction mixture was cooled and the crystalline product which formed (1.95 gm) was collected m.p. 195°-198° C. Evaporation of the reaction solvent and dissolution of the residue in ethyl acetate/acetonitrile which was washed with water, dried ($Na_2SO_4$) and evaporated yielded an additional 0.6 gm from methylene chloride.

Analysis calculated for $C_{10}H_{11}N_3O_3S_2$: C, 42.09; N, 14.73; H, 3.89. Found: C, 42.26; N, 14.74; H, 3.89.

Step B: Preparation of
N,N-Dimethyl-N'-(6-allyloxybenzothiazole-2-sulfonyl)-formamidine A solution of product from Step A (1.14 gm, 4.0 mmol) and allyl bromide (0.5 mL, 5.5 mmol) in dimethyl sulfoxide (8 mL) containing potassium carbonate (0.75 gm, 5.4 mmol) was warmed at 60° C. for 15-20 hours. The reaction mixture was poured into water and the product was extracted into ethyl acetate, dried ($Na_2SO_4$) and evaporated to give a viscous oil (0.92 gm).

Step C: Preparation of
6-Allyloxybenzothiazole-2-sulfonamide

A solution of product from Step B (0.45 gm, 1.4 mmol) in methanol (1.5 mL) was added to 2N sodium hydroxide (2 mL) and stirred at 40° C. for 1 hour. The reaction was poured into water, acidified (HCl), and the product extracted into ethyl acetate. The extract was dried ($Na_2SO_4$) and evaporated to give crude product. Upon trituration of this residue with methylene chloride, the product precipitated and was collected (0.18 gm) and shown to be identical with the product of Example 1.

Employing the procedure substantially as described in Example 1 or 2, but substituting for the allyl bromide used therein an approximately equimolecular amount of a compound of formula R-X, wherein X is halo, $OSO_2CH_3$, $-OSO_2C_6H_5$, $-OSO_2C_6H_4CH_3$, and optionally substituting for the 6-hydroxybenzothiazole-2-sulfonamide, the corresponding 5-hydroxy compound, there are produced the ethers described in Table I in accordance with one of the following processes:

TABLE I

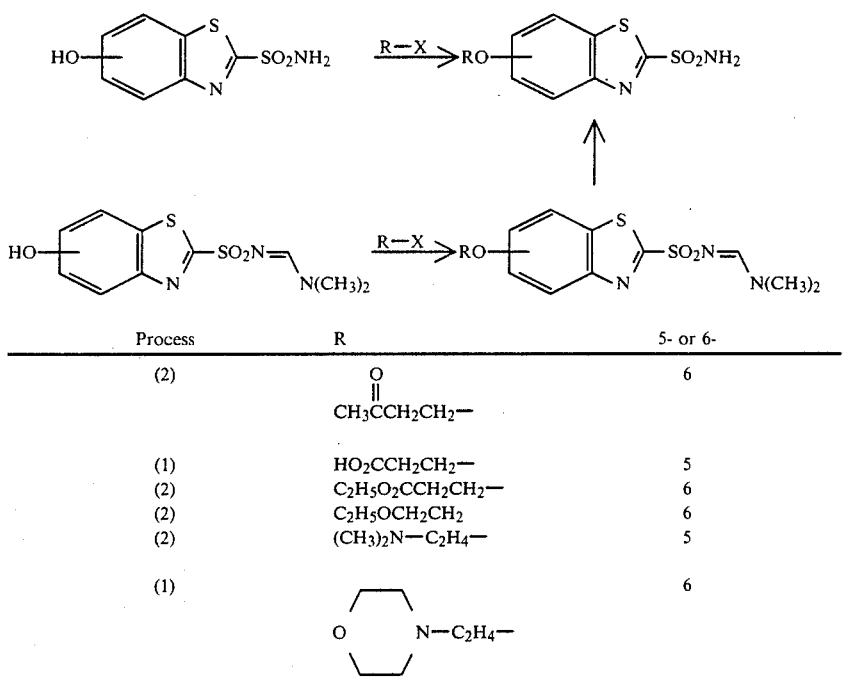

| Process | R | 5- or 6- |
|---|---|---|
| (2) | CH₃CCH₂CH₂— (with O=) | 6 |
| (1) | HO₂CCH₂CH₂— | 5 |
| (2) | C₂H₅O₂CCH₂CH₂— | 6 |
| (2) | C₂H₅OCH₂CH₂ | 6 |
| (2) | (CH₃)₂N—C₂H₄— | 5 |
| (1) | O(  )N—C₂H₄— (morpholino) | 6 |

EXAMPLE 3

6-(2,3-Epoxypropoxy)benzothiazole-2-sulfonamide

Step A: Preparation of 6-[3(2)-Bromo-2(3)-hydroxypropoxy]benzothiazole-2-sulfonamide A solution of 6-allyloxybenzothiazole-2-sulfonamide (5.4 gm, 20 mmol) in DMSO (20 mL) and water (2 mL) was cooled in an ice bath and N-bromosuccinimide (7.5 gm, 42 mmol) was added in one portion. After ½ hour the ice bath was removed and the reaction was stirred at room temperature for 2–5 hours. The reaction was poured into HCl-ice water and the products extracted into ethyl acetate. The extract was dried (Na₂SO₄) and evaporated. The residue was triturated with methylene chloride containing some ethyl acetate and a crystalline mixture of two isomeric products was collected by filtration (4.3 gm).

Anal. calcd. for $C_{10}H_{11}BrN_2O_4S_2$: C, 32.70; N, 7.63; H, 3.02. Found: C, 32.97; N, 7.52; H, 3.01.

Step B: Preparation of 6-(2,3-Epoxypropoxy)benzothiazole-2-sulfonamide

A solution of sodium hydroxide (0.96 gm, 24 mmol) dissolved in methanol (20 mL) was added dropwise to a solution of the isomeric mixture (4.3 gm, 11.7 mmol) from Step A in methanol (15 mL). After stirring at room temperature for one hour, the reaction mixture was poured into HCl-ice water and the crude product extracted into ethyl acetate. This was dried (Na₂SO₄) and evaporated. The resultant residue was triturated with methylene chloride containing some ethyl acetate and crystalline product was collected by filtration (2.1 gm), m.p. 149°–152° C.

Anal. calcd. for $C_{10}H_{10}N_2O_4S_2$: C, 41.94; N, 9.79; H, 3.52. Found: C, 42.29; N, 9.88; H, 3.59.

EXAMPLE 4

6-(2,3-Dihydroxypropoxy)benzothiazole-2-sulfonamide 6-(2,3-Epoxypropoxy)benzothiazole-2-sulfonamide (1.21 gm, 4.25 mmol) was dissolved in ethyl acetate (35 mL) and added to water (25 mL) containing concentrated sulfuric acid (2.5 mL). This two phase mixture was stirred at room temperature overnight and then was poured into water and repeatedly extracted with 5% methanol/ethyl acetate (V/V). The extracts were dried (Na₂SO₄) and evaporated. The residue (1.2 gm) was dissolved in methanol and allowed to sit overnight to give 1.0 gm of impure product. This material was purified by chromatography on silica gel, eluting with 1% methanol/ethyl acetate (V/V). The combined fractions containing product were evaporated and the residue was triturated with methanol to give material which was recrystallized from methanol/ethyl acetate (0.3 gm), m.p. 183°–185° C.

Anal. calcd. for $C_{10}H_{12}N_2O_5S_2$: C, 39.46; N, 9.21; H, 4.07. Found: C: C, 39.69; N, 9.07; H, 4.00.

EXAMPLE 5

6-(3-Methoxy-2-hydroxypropoxy)benzothiazole-2-sulfonamide

A solution of 6-(2,3-epoxypropoxy)benzothiazole-2-sulfonamide (2.15 gm, 7.5 mmol) in methanol (60 mL) containing five drops of concentrated sulfonic acid was stirred at room temperature, monitoring reaction progress by TLC until complete (3 hours). The reaction mixture was poured into ice water and the crude product extracted into ethyl acetate which was dried (Na₂SO₄) and evaporated. The residue was dissolved in a minimum amount of acetonitrile and diluted with chloroform. Upon standing overnight product crystallized (1.8 gm). After several recrystallizations from acetonitrile/chloroform pure product was obtained (1.2 gm), m.p. 153°–155° C.

Anal. calcd. for $C_{11}H_{14}N_2O_5S_2$: C, 41.50; N, 8.80; H, 4.43. Found: C, 41.96; N, 9.06; H, 4.52.

EXAMPLE 6

6-(3-Acetoxy-2-hydroxypropoxy)benzothiazole-2-sulfonamide

A suspension of 6-(2,3-epoxypropoxy)benzothiazole-2-sulfonamide (1.57 gm, 5.5 mmol) in acetic acid (25 mL) was heated at 100° C. for 3–4 hours. The solvent was evaporated. Traces of solvent were removed by chasing with toluene. The residue was dissolved in acetonitrile and diluted with chloroform. Upon standing, product crystallized (0.77 gm), m.p. 173°–175° C.

EXAMPLE 7

6-(3-t-butylamino-2-hydroxypropoxy)benzothiazole-2-sulfonamide

A solution of 6-(2,3-epoxypropoxy)benzothiazole-2-sulfonamide (1.14 gm, 4.0 mmol) in acetonitrile (16 mL) and methanol (4 mL) containing t-butylamine (0.88 mL, 0.4 mmol) was warmed at 50° C. for 15–20 hours. The solvents were evaporated and the residue (1.1 gm) was chromatographed on silica gel eluting with 20–30% methanol/chloroform (V/V). The appropriate fractions were combined and evaporated. The residue was digested in acetonitrile, cooled and the produce collected (0.62 gm), m.p. 195°–196° C.

The following examples of ophthalmic formulations are given by way of illustration.

EXAMPLE 8

| Solution Composition | | |
|---|---|---|
| 6-allyloxybenzothiazole-2-sulfonamide | 1 mg. | 15 mg. |
| Monobasic sodium phosphate.2H$_2$O | 9.38 mg. | 6.10 mg. |
| Dibasic sodium phosphate.12H$_2$O | 28.48 mg | 16.80 mg. |
| Benzalkonium chloride | 0.10 mg. | 0.10 mg. |
| Water for injection q.s. ad. | 1.0 ml. | 1.0 ml. |

The sterile components are added to and dissolved in sterile water. The pH of the suspension is adjusted to 6.8 sterilely and diluted to volume.

EXAMPLE 9

| 6-(2,3-epoxypropoxy)benzothiazole-2-sulfonamide | 5 mg. |
|---|---|
| petrolatum q.s. ad. | 1 gram |

The compound and the petrolatum are aseptically combined.

EXAMPLE 10

| 6-(2,3-dihydroxypropoxy)benzothiazole-2-sulfonamide | 1 mg. |
|---|---|
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (guage) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 11

| 6-(2-hydroxy-3-methoxypropoxy)2-sulfonamide | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 12

| 6-(3-acetoxy-2-hydroxypropoxy)benzothiazole-2-sulfonamide | 1 mg. |
|---|---|
| Hydroxypropyl methyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 13

| 6-2-hydroxy-3-t-butylaminopropoxy)benzothiazole-2-sulfonamide | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (guage) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

What is claimed is:

1. A compound of structural formula:

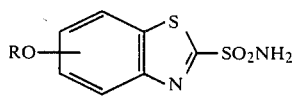

or ophthalmologically acceptable salt thereof wherein R is (1) C$_{1-5}$alkyl substituted with one or more of:

(a) hydroxy,
(b) $C_{1-3}$alkoxy,
(c) halo,
(d)

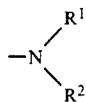

wherein $R^1$ and $R^2$ are independently selected from
(1) hydrogen,
(2) $C_{1-5}$alkyl or
(3) $R^1$ and $R^2$ joined together directly or through a heteroatom selected from O, N or S to form a 5 or 6-membered heterocycle with the nitrogen to which they are attached, wherein the heterocycle is selected from pyrrolidino, piperidino, morpholino and thiazolidino,
(e) $C_{2-4}$alkanoyloxy,
(f) oxiranyl,
(g) carboxy, or
(h) $C_{1-3}$alkoxycarbonyl; or
(2) $C_{2-5}$alkenyl.

2. The compound of claim 1 wherein the R-O-group is in the 6-position.

3. The compound of claim 2 wherein R is
(1) allyl,
(2) 2,3-epoxypropyl,
(3) 2,3-dihydroxypropyl,
(4) 3-methoxy-2-hydroxypropyl,
(5) 3-acetoxy-2-hydroxypropyl, or
(6) 3-t-butylamino-2-hydroxypropyl.

4. An ophthalmic composition comprising an ophthalmologically acceptable carrier and an effective intraocular pressure lowering amount of a compound of structural formula:

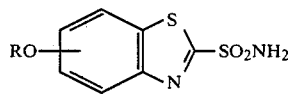

or ophthalmologically acceptable salt thereof wherein R is
(1) $C_{1-5}$alkyl substituted with one or more of:
(a) hydroxy,
(b) $C_{1-3}$alkoxy,
(c) halo,
(d)

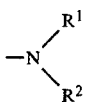

wherein $R^1$ and $R^2$ are independently selected from
(1) hydrogen,
(2) $C_{1-5}$alkyl or
(3) $R^1$ and $R^2$ joined together directly or through a heteroatom selected from O, N or S to form a 5 or 6-membered heterocycle with the nitrogen to which they are attached, wherein the heterocycle is selected from pyrrolidino, piperidino, morpholino, and thiazolidino,
(e) $C_{2-4}$alkanoyloxy,
(f) oxiranyl,
(g) carboxy, or
(h) $C_{1-3}$alkoxycarbonyl; or
(2) $C_{2-5}$alkenyl.

5. The composition of claim 4 wherein the R-O-group is in the 6-position.

6. The composition of claim 5 wherein R is
(1) allyl,
(2) 2,3-epoxypropyl,
(3) 2,3-dihydroxypropyl,
(4) 3-methoxy-2-hydroxypropyl,
(5) 3-acetoxy-2-hydroxypropyl, or
(6) 3-t-butylamino-2-hydroxypropyl.

7. A method of treatment of elevated intraocular pressure which comprises the administration to a patient in need of such treatment of an effective intraocular pressure lowering amount of a compound of structural formula:

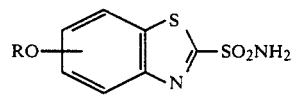

or ophthalmologically acceptable salt thereof wherein R is
(1) $C_{1-5}$alkyl substituted with one or more of:
(a) hydroxy,
(b) $C_{1-3}$alkoxy,
(c) halo,
(d)

wherein $R^1$ and $R^2$ are independently selected from
(1) hydrogen,
(2) $C_{1-5}$alkyl or
(3) $R^1$ and $R^2$ joined together directly or through a heteroatom selected from O, N or S to form a 5 or 6-membered heterocycle with the nitrogen to which they are attached, wherein the heterocycle is selected from pyrrolidino, piperidino, morpholino, and thiazolidino,
(e) $C_{2-4}$alkanoyloxy,
(f) oxiranyl,
(g) carboxy, or
(h) $C_{1-3}$alkoxycarbonyl; or
(2) $C_{2-5}$alkenyl.

8. The method of claim 7 wherein the R-O-group is in the 6-position.

9. The method of claim 8 wherein R is
(1) allyl,
(2) 2,3-epoxypropyl,
(3) 2,3-dihydroxypropyl,
(4) 3-methoxy-2-hydroxypropyl,
(5) 3-acetoxy-2-hydroxypropyl, or
(6) 3-t-butylamino-2-hydroxypropyl.

* * * * *

Adverse Decision in Interference

In Interference No. 101,699, involving Patent No. 4,505,923, J. M. Hoffman, Jr., O. W. Woltersdorf, Jr., ETHERS OF HYDROXYBENZOTHIAZOLE-2-SULFONAMIDE FOR THE TOPICAL TREATMENT OF ELEVATED INTRAOCULAR PRESSURE, final judgment adverse to the patentee was rendered February 20, 1990, as to claims 1-9.
*[Official Gazette August 28, 1990]*